(12) United States Patent
Samadani et al.

(10) Patent No.: US 10,729,321 B2
(45) Date of Patent: Aug. 4, 2020

(54) EYE TRACKING SYSTEM

(71) Applicant: Oculogica Inc, New York, NY (US)

(72) Inventors: Rosina Samadani, New York, NY (US); Daniel O. Sanderson, New Richmond, WI (US)

(73) Assignee: OCULOGICA INC., New York, NY (US)

( * ) Notice: Subject to any disclaimer, the term of this patent is extended or adjusted under 35 U.S.C. 154(b) by 114 days.

(21) Appl. No.: 16/129,187

(22) Filed: Sep. 12, 2018

(65) Prior Publication Data

US 2019/0076016 A1    Mar. 14, 2019

Related U.S. Application Data

(60) Provisional application No. 62/558,069, filed on Sep. 13, 2017.

(51) Int. Cl.
| | |
|---|---|
| *A61B 3/113* | (2006.01) |
| *G06F 3/01* | (2006.01) |
| *A61B 3/00* | (2006.01) |
| *A61B 5/16* | (2006.01) |
| *A61M 21/00* | (2006.01) |

(52) U.S. Cl.
CPC ........... *A61B 3/113* (2013.01); *A61B 3/0033* (2013.01); *A61B 3/0041* (2013.01); *A61B 5/163* (2017.08); *G06F 3/013* (2013.01); *A61M 2021/005* (2013.01); *A61M 2021/0027* (2013.01)

(58) Field of Classification Search
CPC ...................................................... A61B 3/113
USPC ...................................................... 351/209
See application file for complete search history.

(56) References Cited

U.S. PATENT DOCUMENTS

| | | | |
|---|---|---|---|
| 6,961,448 B2 | 11/2005 | Nichols et al. | |
| 7,496,174 B2 | 2/2009 | Gertner et al. | |
| 7,703,921 B2 | 4/2010 | Dick et al. | |
| 7,792,249 B2 | 9/2010 | Gertner et al. | |

(Continued)

FOREIGN PATENT DOCUMENTS

| | | |
|---|---|---|
| WO | 2007/075460 A2 | 7/2007 |
| WO | WO2013148557 | 10/2013 |

(Continued)

OTHER PUBLICATIONS

International Search Report and Written Opinion for Application No. PCT/US2018/050650 dated Nov. 30, 2018.

*Primary Examiner* — James C. Jones
(74) *Attorney, Agent, or Firm* — Wei & Sleman LLP

(57) ABSTRACT

A system for measuring eye tracking may include a chassis, which may include a main column and a head rest assembly. The head rest assembly may include a stimulus screen for displaying a video to the patient, an optical mirror, an eye tracking camera, and at least one head rest member for stabilizing the patient's head, relative to the stimulus screen. The system may also include: a base attached to a bottom of the main column to support the main column; an arm extending from the main column to support the head rest assembly; a touchscreen interface attached to the main column and configured to provide control of the system to a user; a camera computer housed in the main column for controlling the eye tracking camera; and a system computer housed in the main column for controlling the stimulus screen, data processing and other functions.

19 Claims, 13 Drawing Sheets

(56) References Cited

U.S. PATENT DOCUMENTS

| | | |
|---|---|---|
| 8,732,795 B2 | 5/2014 | Skeel et al. |
| 9,101,312 B2 | 8/2015 | Waldorf et al. |
| 9,229,227 B2 | 1/2016 | Border et al. |
| 9,265,416 B2 * | 2/2016 | Klin ........................ A61B 3/032 |
| 9,439,592 B2 | 9/2016 | Stack et al. |
| 9,459,451 B2 | 10/2016 | Saarikko |
| 9,642,522 B2 | 5/2017 | Samadani et al. |
| 10,201,274 B2 | 2/2019 | Samadani et al. |
| 2001/0056359 A1 | 12/2001 | Abreu |
| 2013/0144185 A1 | 6/2013 | Fuller |
| 2013/0208952 A1 | 8/2013 | Auchinleck |
| 2013/0278899 A1 | 10/2013 | Waldorf |
| 2015/0190050 A1 | 7/2015 | Samadani et al. |
| 2015/0326570 A1 | 11/2015 | Publicover et al. |
| 2016/0278716 A1 | 9/2016 | Samadani |
| 2017/0091392 A1 | 3/2017 | White et al. |
| 2017/0135577 A1 | 5/2017 | Komogortsev |
| 2017/0172408 A1 | 6/2017 | Samadani et al. |
| 2017/0364732 A1 | 12/2017 | Komogortsev |
| 2017/0367633 A1 | 12/2017 | Samadani et al. |
| 2018/0092531 A1 | 4/2018 | Samadani et al. |
| 2018/0110410 A1 | 4/2018 | Samadani et al. |
| 2018/0116512 A1 | 5/2018 | Bitoun |
| 2018/0235530 A1 | 8/2018 | Samadani et al. |
| 2018/0279877 A1 | 10/2018 | Berdahl et al. |

FOREIGN PATENT DOCUMENTS

| | | |
|---|---|---|
| WO | WO2014204904 | 12/2014 |
| WO | 2015/057321 A1 | 4/2015 |
| WO | 2016/118453 A1 | 7/2016 |

* cited by examiner

EYE TRACKING SYSTEM

CROSS-REFERENCE TO RELATED APPLICATIONS

This application claims the benefit of U.S. Provisional Patent Application No. 62/558,069, filed Sep. 13, 2017, entitled, "EYE TRACKING SYSTEM." The disclosure of this priority application is hereby incorporated by reference in its entirety into the present application.

TECHNICAL FIELD

This application is directed to medical devices, systems and methods. More specifically, the application is directed to eye tracking devices, systems and methods.

BACKGROUND OF THE INVENTION

Many central nervous system injuries and abnormalities can be challenging to diagnose and localize within the nervous system. The assignee of the present application has developed methods and systems that use eye tracking measurement to help diagnose and/or localize a number of different central nervous system injuries and abnormalities, such as but not limited to increased intracranial pressure, concussion, reduced or impaired cranial nerve function, and the like. Some of these methods and systems are described in U.S. Pat. No. 9,642,522 and U.S. Patent Application Pub. Nos. 2016/0278716 and 2017/0172408, all of which are hereby incorporated herein by reference.

BRIEF DESCRIPTION OF THE DRAWINGS

FIG. 6 is a screen shot of new patient display for a touchscreen interface of an eye tracking system, according to one embodiment;

DETAILED DESCRIPTION OF THE INVENTION

Figure 1A:
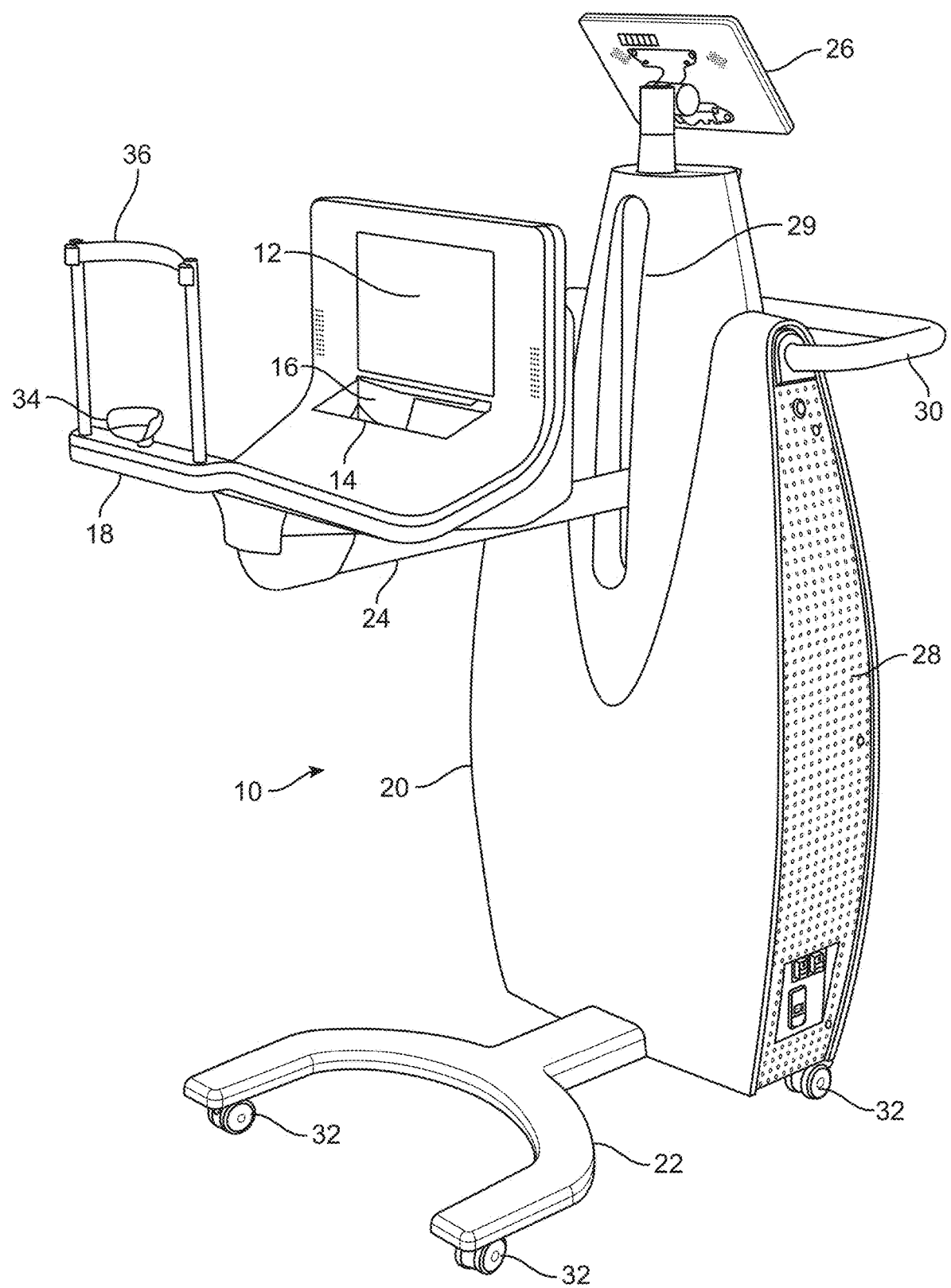
FIGS. 1A-1C are patient-facing, side, and technician-facing views, respectively, of a system for measuring eye tracking, according to one embodiment.
Figure 1B:
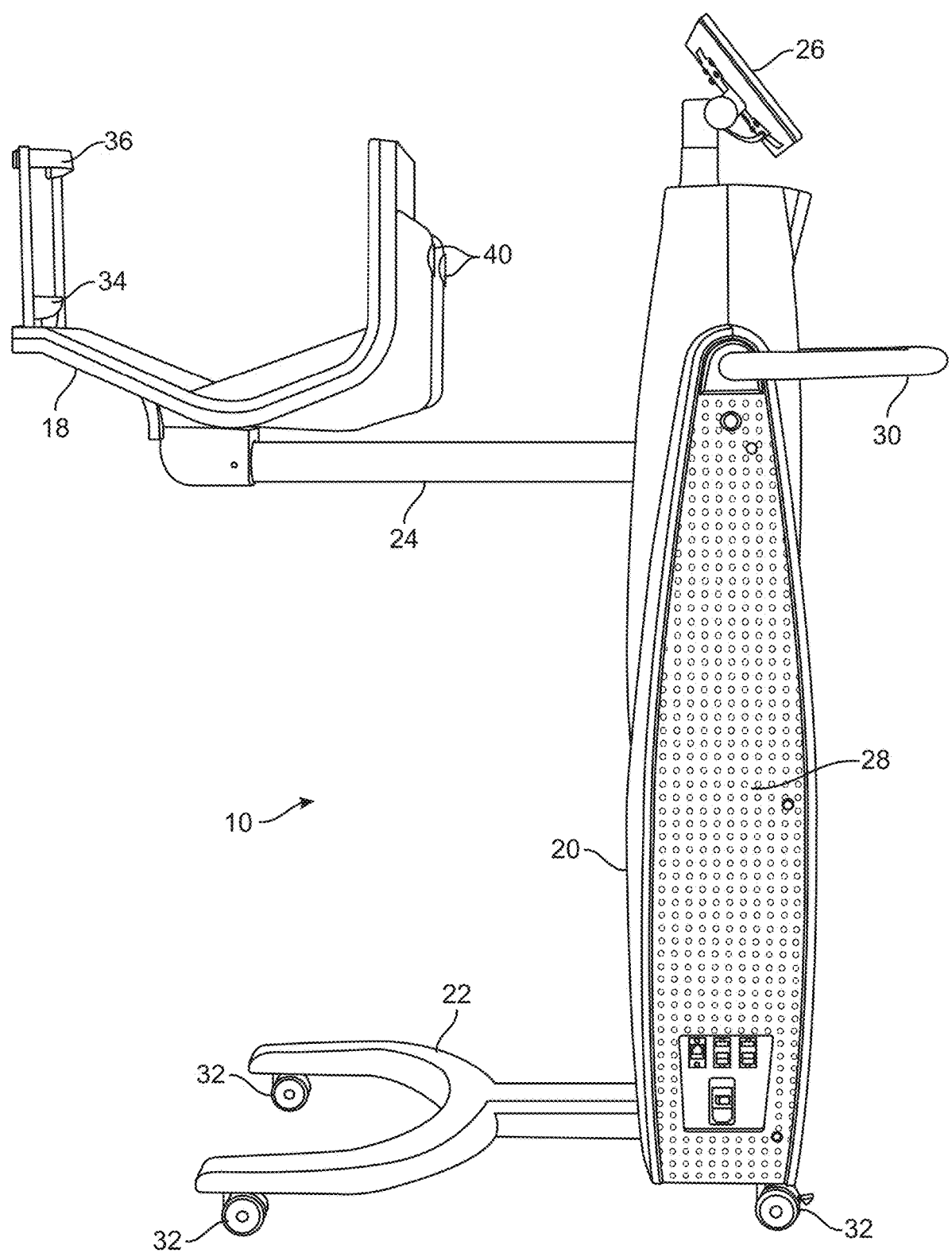

Referring to FIGS. 1A-1C, 2A-2B and 3, an eye tracking and diagnostic system 10 is illustrated, according to one embodiment. System 10 is used to track a patient's eye movement and diagnose one or more eye movement abnormalities. In some embodiments, system 10 includes at least one processor, which may further analyze data related to the eye movement abnormalities to help diagnose and/or localize a neurological injury or abnormality, such as but not limited to increased intracranial pressure, concussion, reduced or impaired cranial nerve function. In use, a stimulus video is presented on system's 10 LCD stimulus screen 12, and the patient's eye movement is tracked over time by an infrared eye tracking camera 14. Fixed orientation of the patient's head, relative to the stimulus screen 12 and camera 14, is ensured by a head rest assembly 18, which adjusts to a seated or supine patient. System 10 is operated from a touchscreen interface 26. System 10 is coupled together via a wheeled chassis 20 suitable for wheeling to the examination location.

Figure 1C:
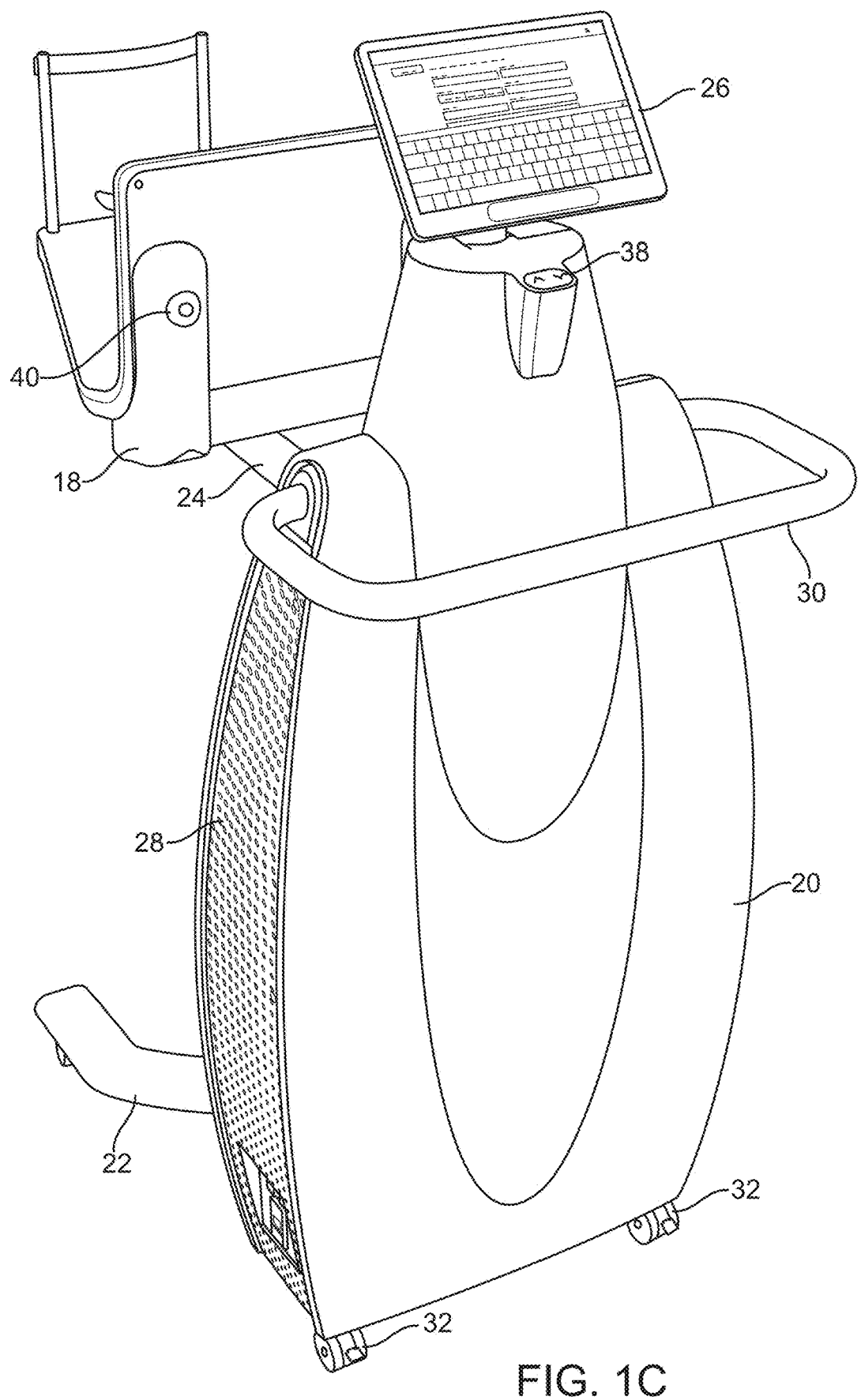
Figure 2A:
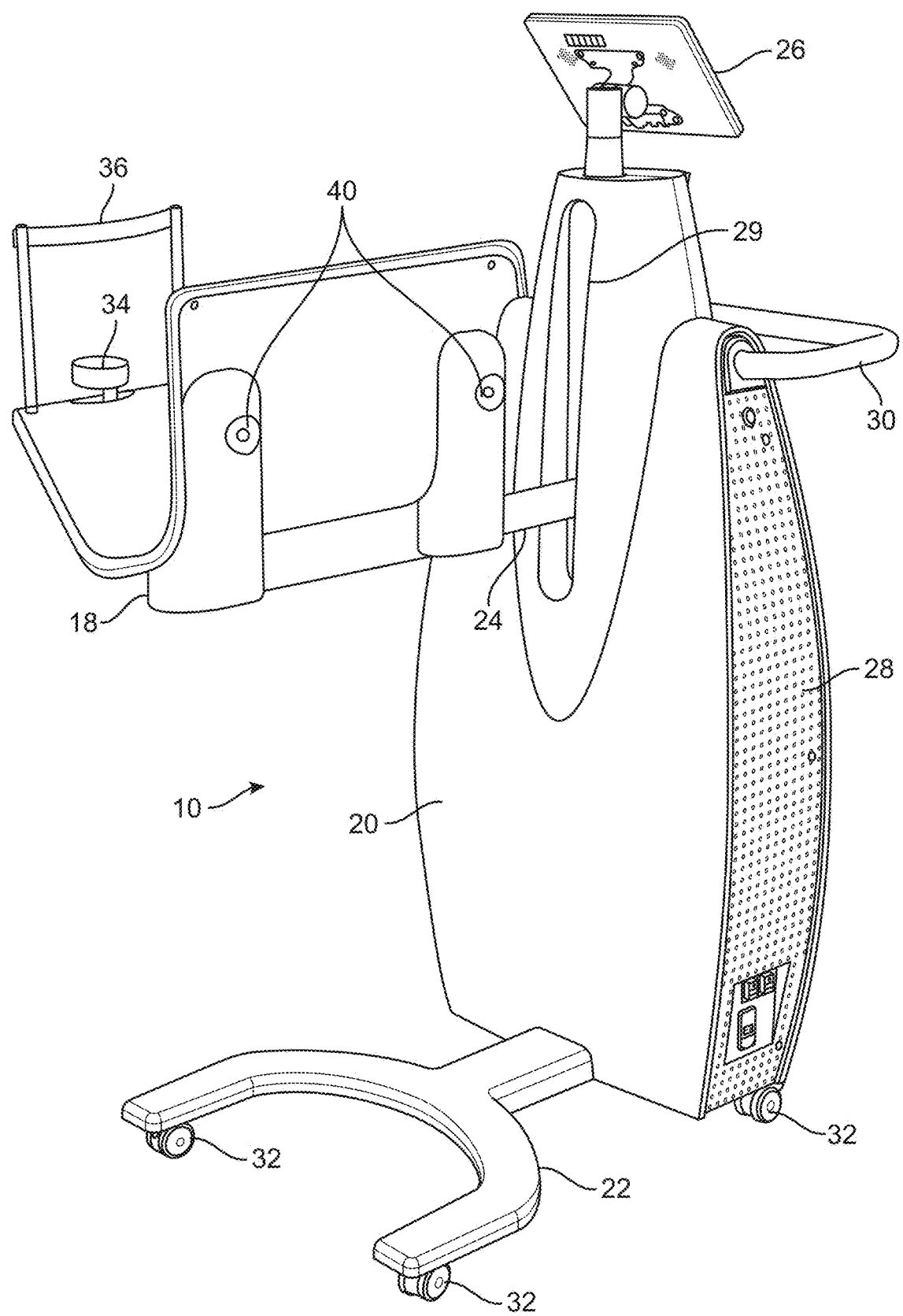
FIGS. 2A and 2B are patient-facing perspective views of the system of FIGS. 1A-1C, illustrating adjustability of a head rest assembly portion of the system in a horizontal plane (FIG. 2A) and a vertical plane (FIG. 2B)
Figure 2B:
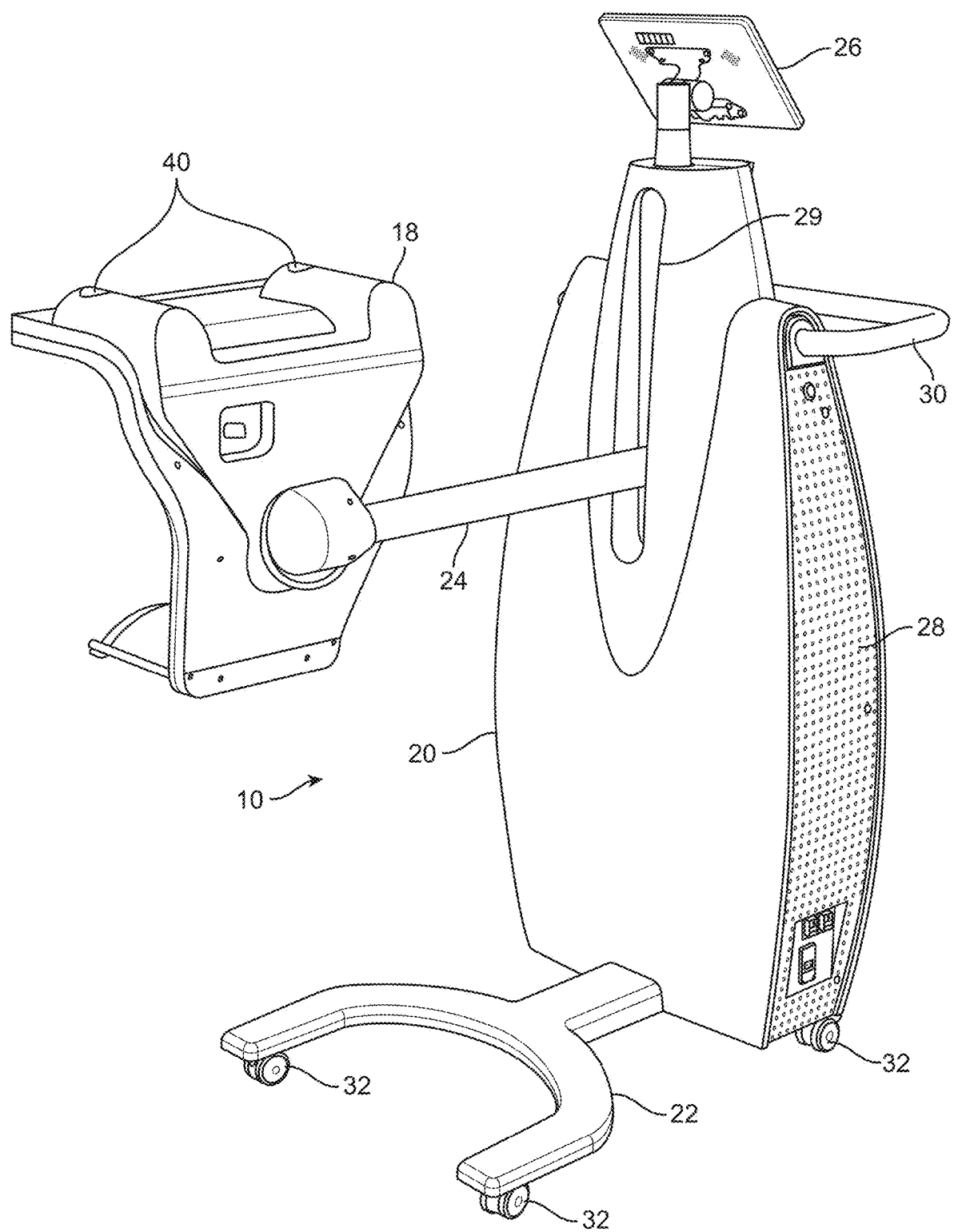
Figure 3:
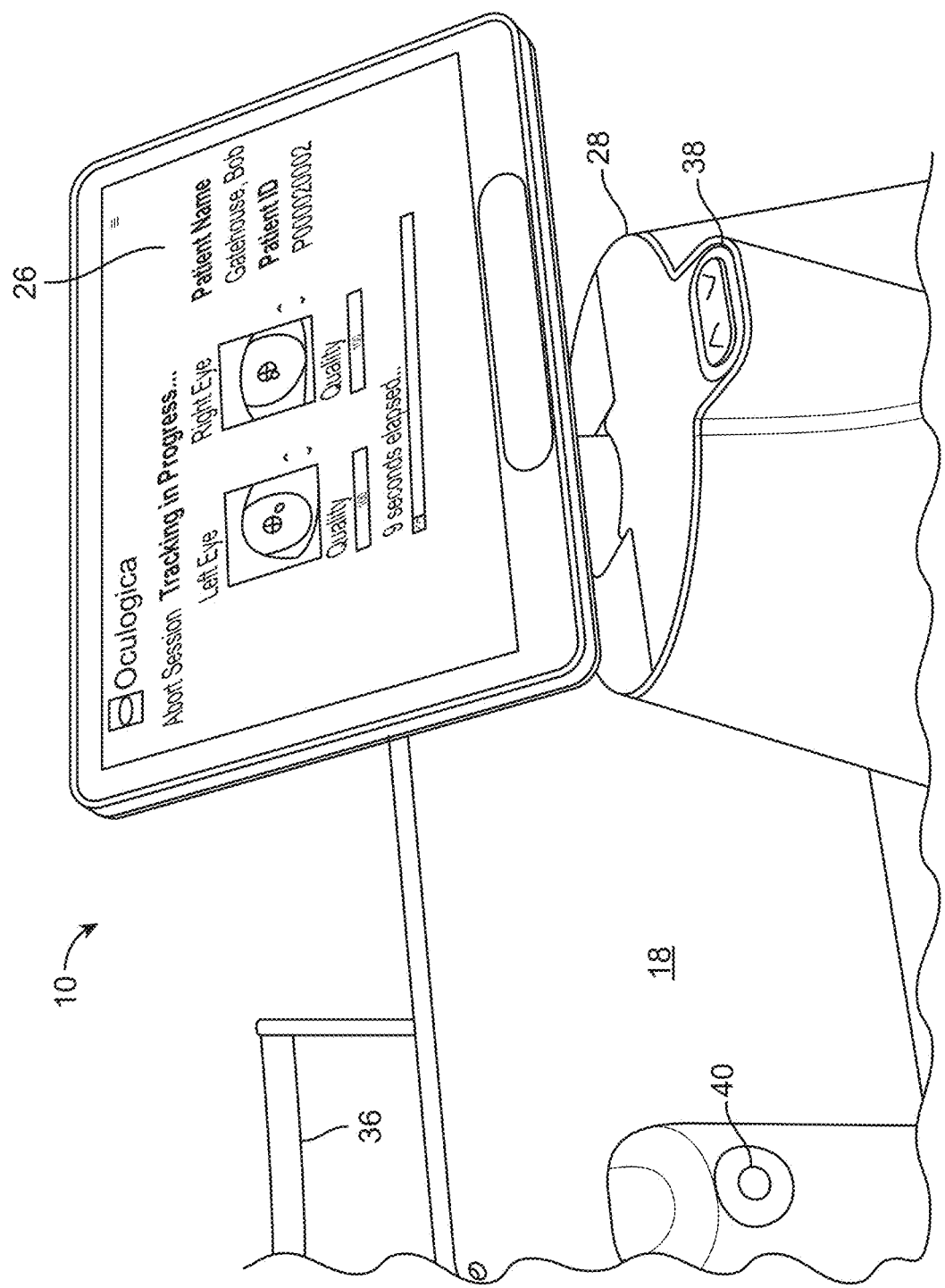
FIG. 3 is a close-up view of a touchscreen interface of the system of FIGS. 1A-2B.

Chassis 20 includes two main parts: a main column 28 supported by a base 22, and a head rest assembly 18. Head rest assembly 18 is supported on an arm 24, which can be raised and lowered using an electrically-driven elevator in main column 28, controlled by an up/down button 38 (FIGS. 1C and 3). Arm 24 moves up and down through a vertical slot 29 (FIGS. 1A, 2A, 2B) in main column 28. Four locking castors 32 in base 22 allow the entire unit to be moved, with base 22 being sized to fit underneath a patient bed or gurney. A handle 30 on main column 28 is used to push and/or pull system 10 into place.

In one embodiment, main column 28 houses two computers, a power supply, the elevator mechanism, an isolation transformer, and other electrical parts, none of which is visible in the figures. Operator touchscreen interface 26 (also called "operator console 26" herein) is located on main column 28.

Head rest assembly 18 includes a chin rest 34 and a forehead rest 36, to stabilize the patient's head, stimulus screen 12, an optical mirror 16 used to fold the optical path allowing for more compact casing, and a high-speed eye tracking camera 14. As shown in FIGS. 2A and 2B, the entire head rest assembly 18 can be rotated in the horizontal plane 90 degrees in either direction, for a total horizontal rotation of 180 degrees (FIG. 2A), and up to 90 degrees in the vertical direction downward to accommodate supine patients (FIG. 2B). In the illustrated embodiment, there are several discrete positions within the vertical rotation where head rest assembly 18 locks into place. Buttons 40 on the back of head rest assembly 18 activate solenoids, so assembly 18 can be rotated vertically and then locked.

A standard 110-volt medical grade cord may provide power to system's 10 elevator mechanism and a 400-watt power supply. The power supply provides regulated DC power to the computers, as well as the solenoid controls in head rest assembly 18.

System 10 includes two computers, which are housed in main column 28 of chassis 20 and thus not visible in the figures. A camera computer, which may be provided by the same manufacturer as the manufacturer of camera 14, may run the real-time software for camera 14 under a real-time operating system. It detects eye motion events, such as saccades, blinks, and fixations, and computes the gaze coordinates for each eye at 500 Hz, storing the raw data until it is needed by the application. The application computer may be a small form-factor PC that runs a system application for system 10. The system application provides the user interface, controls the logic flow, displays the stimulus video, processes the raw data from the camera computer, and stores results in persistent storage.

The user interacts with the system application through touchscreen interface 26. Stimulus screen 12 (the second monitor on system 10) displays the stimulus media to the patient. Two built-in speakers provide the audio for the stimulus media.

In some embodiments, the processor(s) in system 10 is configured to generate a score describing a patient's eye tracking ability. For example, in one embodiment, system 10 generates a score ranging from 0-20, where the score is interpreted as a binary classification for eye movement abnormalities, and where anything equal to or greater than 10 is a positive result (abnormality present) and everything below 10 is negative (no abnormality). The system's 10 operating algorithm identifies eye tracking abnormalities and computes the score.

Eye Tracking Camera

In one embodiment, eye tracking camera 14 is an EyeLink 1000 Plus USB (SR Research, Ottawa, Canada) and is used to capture the eye movements of the patient. Camera 14 captures 500 frames of gaze data per second for each eye, with an average accuracy of 0.25 to 0.5 degrees. The illuminators are infrared, and it uses dark pupil eye tracking, in which the infrared sources are offset from camera 14. This technique typically provides better results across ethnicities and varied lighting conditions. The gaze tracking ranges up to 32 degrees horizontally and 25 degrees vertically. The distance between the subject's eyes and the camera is 52 cm. The specifications for camera 14, as provided by the vendor, are shown in Table 1.

TABLE 1

EyeLink Camera Specifications

| Spec | Description |
| --- | --- |
| Average accuracy of gaze coordinate data | Down to 0.15 degrees (0.25 degrees to 0.5 degrees typical) |
| sampling rate | Binocular: 250, 500 hz |
| End-to-end sample delay | m < 1.8 msec, sd < 0.6 msec @ 1000 hz |
| Blink/occlusion recovery | m < 1.8 msec, sd < 0.6 msec @ 1000 hz |
| Spatial resolution | <0.01 degrees rms |
| Eye tracking principle | Dark pupil - corneal reflection |
| Pupil detection models | Centroid or ellipse fitting |
| Pupil size resolution | 0.2% of diameter |
| Gaze tracking range | 32 degrees horizontally, 25 degrees vertically |
| Allowed head movements without accuracy reduction | ±25 mm horizontal or vertical6, ±10 mm depth |
| Optimal camera-eye distance | Between 40-70 cm |
| Glasses compatibility | The user must remove their glasses to use the system |
| On-line event parsing | Fixation/saccade/blink/fixation update |
| Real-time operator feedback | Eye position cursor or position traces. Camera images and tracking status. |

Eye Tracking Computer

As mentioned above, in one embodiment, camera 14 is driven by a dedicated real-time computer running the QNX operating system. The specifications for this eye tracking computer are shown in Table 2.

TABLE 2

EyeLink Computer Specifications

| Spec | Description |
| --- | --- |
| Design | Pico form factor; 8-layer SBC PCB size: 100 mm × 72 mm |
| Embedded CPU | Intel Braswell SoC CPU |
| Memory | Onboard 4 GB unbuffered DDR3L 1600 MHz DRAM |
| Expansion slot | 1 full-size mini-PCIE slot |
| Storage | SATA III port M.2 M-key 2242 slot |
| LAN chip | Integrated with Intel i211AT PCI-E Gigabit LAN chip Support fast Ethernet LAN function of providing 10/100/1000 Mbps Ethernet data transfer rate |
| Audio chip | Realtek ALC662 2-CH HD audio codec integrated Audio driver and utility included |
| BIOS | 64 Mbit flash ROM |
| Rear I/O | 12 V DC-in power jack USB 3.0 port (2) Display port RJ-45 LAN port |
| Internal I/O | 2-pin internal 12 V DC-in power connector SATA power-out connector Front panel audio header 9-pin USB 2.0 header Serial port header (2) Front panel header LAN LED activity header LVDS header LVDS inverter |

System Application Computer

As mentioned above, in one embodiment, the system application runs on a mini-ITX board running Windows 10 Pro, configured as a kiosk device. The specifications are shown in Table 3.

TABLE 3

System Application Computer Specifications

| Spec | Description |
| --- | --- |
| Design | Mini ITX form factor |
| CPU | Intel i7 (speed, etc TBD) |
| Chipset | Intel H170 |
| Memory | 16 GB dual channel DDR4 |
| Expansion slot | PCI Express 3.0 × 16 slot Vertical half-size mini-PCI Express slot |
| Graphics | Intel HD graphics, dual graphics output, DVI/HDMI max resolution to 4K × 2K |
| Additional graphics | Invidia GeForce 210, DVI/VGA/DisplayPort max resolution to 2560 × 1600 |
| Audio | 7.1 CH HD audio |
| LAN | Intel 1219V (gigabit LAN) Realtek RTL8111H (gigabit LAN) |
| Rear I/O | PS/2 mouse/keyboard port DVI port HDMI port USB 2.0 ports (2) USB 3.0 ports (6) RJ-45 LAN ports (2) HD audio jack |
| Storage | SATA 3 256 GB SSD |
| BIOS | 128 MB AMI UEFI legal BIOS |
| Certifications | FCC, CE, WHQL |

Stimulus Display

Stimulus screen 12, according to one embodiment, is used to display a video that may last any suitable length of time, such as 220 seconds in one embodiment. In one embodiment, the only purpose of stimulus screen 12 is to display the visual stimulus. The video may be one of several pre-determined videos. These videos may include music videos, clips from children's movies, sports clips, talent performances, "reality TV" clips, etc. The choice of videos may be designed to appeal to a broad group of subjects. Users of the device may choose which video to display or may ask the patient which one they would like to watch. Additional media selections may be downloaded via a UBS drive, for example. In one embodiment, the video aperture is square, with each side being approximately ¼ the width of the visible display. The trajectory of the displayed video around stimulus screen 12 follows a predefined discrete path, such as 5 cycles along the perimeter of stimulus screen 12 with a velocity of 10 seconds per side, according to one embodiment. In one embodiment, stimulus screen 12 is an GeChic 1303 monitor, with the specifications shown below in Table 4.

TABLE 4

Stimulus Screen Specifications

| Spec | Description |
| --- | --- |
| Aspect ratio | 1.78:1 |
| Maximum resolution | 1920 × 1080 |
| Screen size | 13.3 inches |
| Display type | LED |
| Viewing angle | 89°/89°/89°/89° |
| Contrast ratio | 700:1 |
| Power input | 5 V, 2.0 A |

Touchscreen Interface

Touchscreen interface 26 (which may also be referred to as an "operator console" or simply "touchscreen") is used by the technician to interact with the system application. In the pictured embodiment, touchscreen interface 26 includes only a touch screen display, meaning that there is no keyboard or other input device. Of course, alternative embodiments may include a keyboard or other input device(s). In one embodiment, touchscreen interface 26 may be a Mimo UM-1080CH-G, with the specifications set forth below in Table 5.

TABLE 5

Touchscreen Interface Specifications

| Spec | Description |
| --- | --- |
| Capacitive touchscreen | Yes |
| Maximum resolution | 1280 × 800 |
| Screen size | 10.1 inches |
| Viewing angle | 170° × 170° |
| Contrast ratio | 800:1 |
| Power input | 6 W |

Head Rest Assembly

Chin rest 34 and forehead rest 36 are used to stabilize the user's head and maintain appropriate distance from stimulus screen 12 during eye tracking. Chin rest 34 may be made from the non-toxic, non-hazardous biodegradable plastic Bakelite resin (polyoxybenzylmethyleneglycolanhydride), and forehead rest 36 may be constructed from aluminum covered with a thin EPDM (ethylene propylene diene terpolymer) foam pad blended with neoprene and SBR (styrene-butadiene rubber) pad with closed-cell construction, to resist liquid, solid, and gas absorbance. Both surfaces may be wiped using sterile alcohol swabs before and after each use.

System Calibration

The calibration information below in Table 6 applies to the components of system, according to one embodiment.

TABLE 6

System Calibration

| Component | Calibration notes |
| --- | --- |
| Eye tracking camera 14 | A focus knob on the bottom of the unit adjusts focus. Once it is set, it generally does not need any adjustment unless the knob is accidentally jarred. The user guide provides instructions for adjusting focus. Gaze point calibration is not required. System 10 uses camera's 14 built-in default calibration for calculating gaze points from pupil detection and corneal reflection measurements. |
| Stimulus display 12 | Stimulus display 12 is surrounded by bezels to reduce the size of display 12 to effectively be 4:3 instead of 1.78:1. The software uses calibration information stored in the device configuration file to determine what part of the display is actually visible to the user. The configuration, once set, does not change since the bezels and display are fixed. These configuration parameters will be set at the factory before being shipped to the end user. |
| Operator console 26 | The aspect ratio will be set when the unit is assembled. No additional calibration by the user is needed. |
| Computers | The computers perform a boot sequence upon startup that will run diagnostic procedures to ensure correct operation. No additional calibration of the computers is necessary. |
| Head rest assembly 18 rotation | At assembly time, the head rest assembly 18 rotation limits are set and fixed into place. No additional calibration is needed. |
| Chin rest 34 and forehead rest 36 | The user should use an alcohol wipe before and after each patient in order to sterilize the parts of the device that come in contact with the patient. Instructions for this are included in the user guide. |
| Elevator | At assembly time, the elevator height limits are set and fixed into place. No additional calibration is needed. The elevator is not expected to require any maintenance during the normal lifetime of the device. |
| Optical mirror 16 | Dust or dirt may accumulate in the camera/mirror bay of head rest assembly 18. User guide instructions provide information about how to remove the debris using compressed air if needed. |

Principle of Operation

System 10 measures a patient's eye tracking while watching a video move around stimulus screen 12 and then analyzes the data from the eye tracking measurements, using an algorithm, to extract clinically relevant eye measures by using temporal assessment. The patient watches a video moving inside an aperture with a set trajectory for 220 seconds (in one embodiment) at a fixed distance from stimulus screen 12. The position of each pupil is recorded over time elapsed, as the video travels on its time course, enabling detection of impaired ability to move the eyes relative to time and therefore relative to each other. The algorithm inputs are measurements of the individual (left and right) eye-movements, averaged over the five cycles that the eyes move while watching the 220-second video that plays in an aperture moving around screen 12. In one embodiment, the algorithm output is a "BOX Score," calculated by multiplying multiple constants with different individual parameters, and summing those factors.

Method Overview

According to one embodiment, a brief summary of the key steps for use of system 10 is provided below.
1. Log in with user name and password. The user's login is validated against cached credentials.
2. Fill in patient information fields (name, DOB, gender, etc.). The patient data will be cached locally.
3. Select the video to be shown by tapping its thumbnail icon.
4. In the next screen, an image of the patient's face is shown with visual clues of where the camera is looking for the pupils and whether the pupils can be detected.

5. Tap on each eye to instruct the software to lock the pupil positions.
6. Illumination is defaulted at 75%, but it can be set to 50% or 100% depending on ambient lighting.
7. Optional: Ask subject to look at the corners of the stimulus screen to ensure pupil capture at all points.
8. Tap the Start button to initiate the eye tracking.
9. While the eye tracking is in progress, make sure the eyes remain locked most of the time. Quality indicators show how what percentage data is being collected for each eye over the last 15 seconds.
10. Upon completion, system 10 processes the results and displays a report screen. Green value for BOX score indicates that metric fell within normal bounds. Red indicates outside normal.
11. Elect to save and exit, save and re-do, discard and exit, or discard and re-do.
12. Complete.

System Computer Processing Overview

Central to the operation of system 10 is how the software processes raw gaze data from the eye tracking camera and calculates a BOX score. An overview of this process is outlined below.

1. During a tracking, system 10 collects 220 seconds of binocular gaze data at 500 Hz as the patient watches the video stimulus go around screen 12 five times. The trajectory is as follows:
   a. The stimulus starts in the upper left corner and remains stationary for 10 seconds.
   b. The stimulus moves around the outer edges of the stimulus screen in a clockwise fashion, taking ten seconds for each side or 40 second for each cycle. The stimulus makes five cycles plus one extra side along the top for a total of 220 seconds.
2. The first and last ten seconds of data are discarded.
3. The processing first removes blink data. These data become "NaN's" (not a number) in the processing and are ignored in all subsequent processing.
4. Next, the gaze data are normalized, and several dozen metrics are computed from the normalized data, which characterize the patient's tracking. Some of the metrics are conjugate values that evaluate the differences between the left and right eye.
5. The most correlated metrics are then fed into a polynomial formula that produces a BOX score between 0 and 20. Scores less than 10 are considered normal.
6. The algorithm also computes a quality score (1 to 10 with 10 being the best) based on the percentage of NaN's that were in the raw data.

Figure 4:
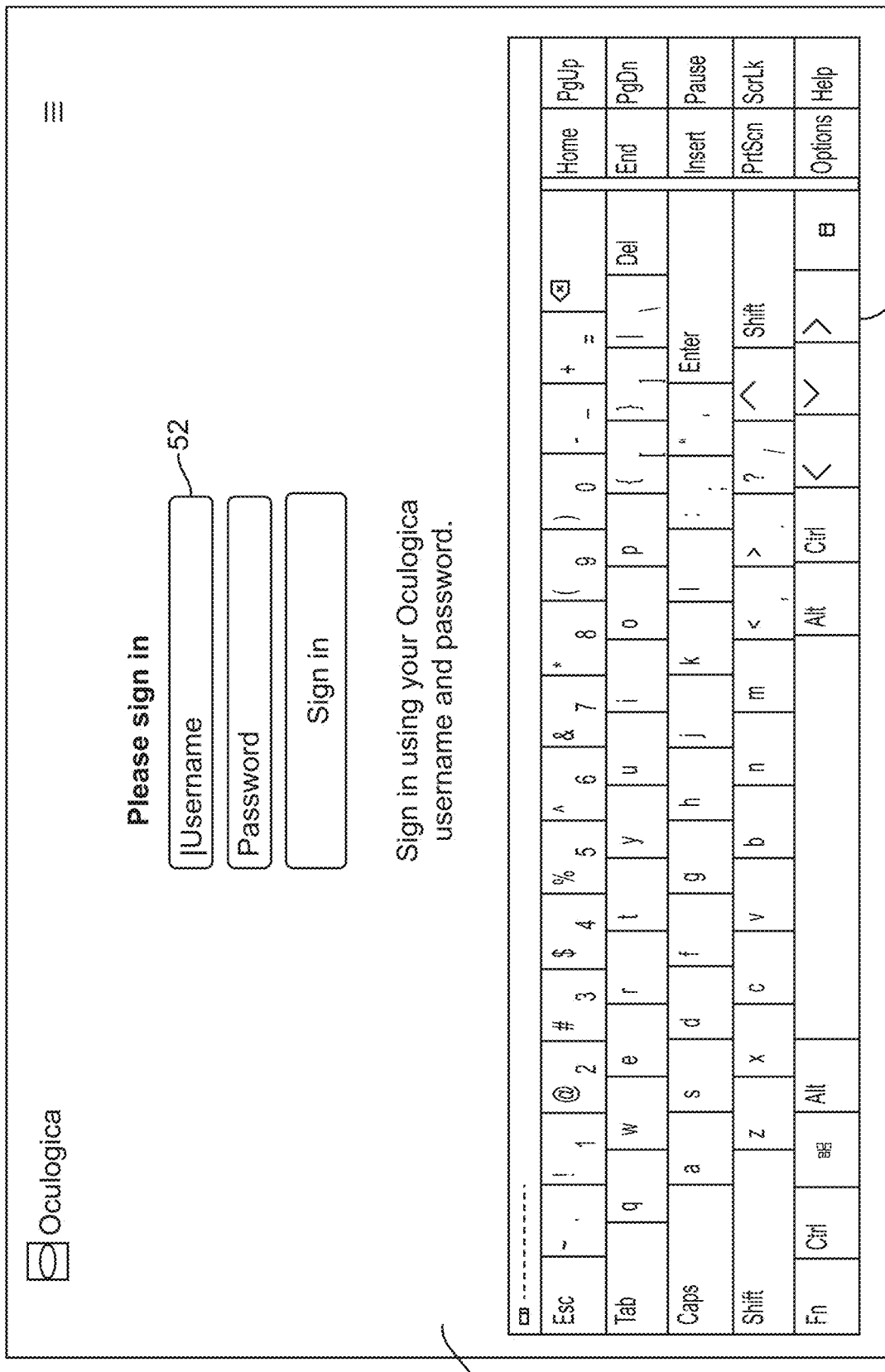
FIG. 4 is a screen shot of a sign-in display for a touchscreen interface of an eye tracking system, according to one embodiment.

Referring now to FIG. 4, one embodiment of a sign-in display 50, which may be shown on touchscreen interface 26, is illustrated. Sign-in display 50 includes a user sign-in area 52 and a touchscreen keyboard area 54, the latter of which represents a standard keyboard on the touchscreen interface 26. The technician or other user of system 10 may sign in on this page, using keyboard 54.

Figure 5:
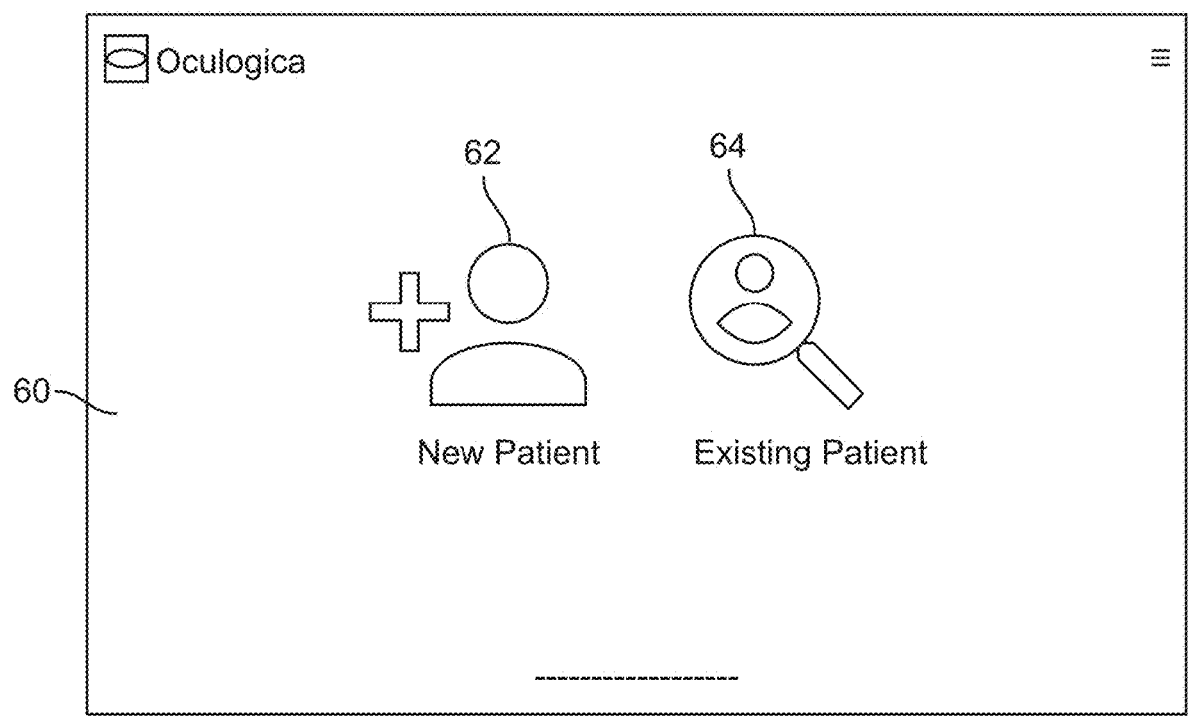
FIG. 5 is a screen shot of a patient selection display for a touchscreen interface of an eye tracking system, according to one embodiment.

FIG. 5 illustrates a patient selection display 60, which may be presented to the user after sign-in. Patient selection display 60 may include a new patient button 62 and an existing patient button 64, which the user may use to select whether to enter information for a new patient or an existing patient.

Figure 6:
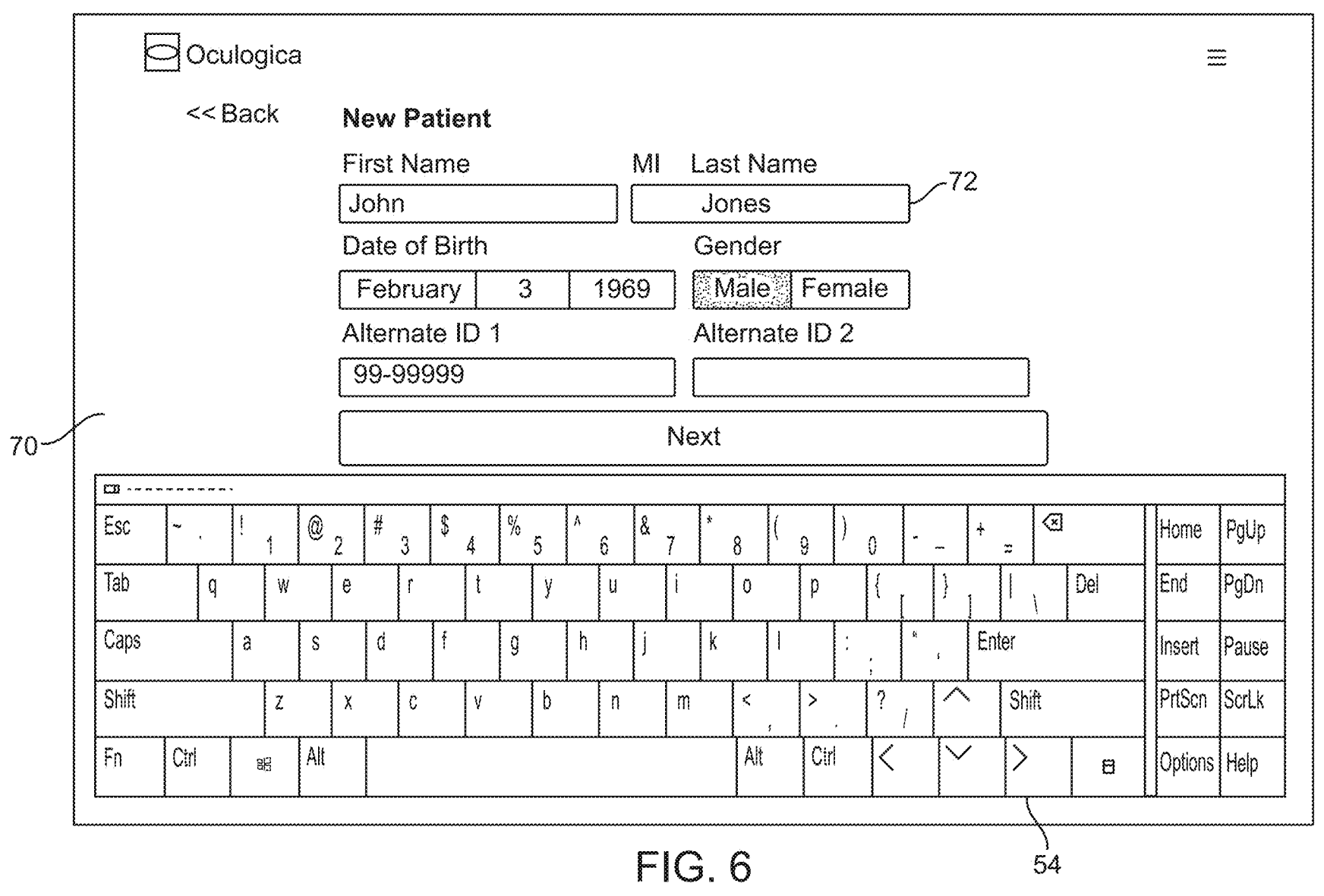

Referring to FIG. 6, a new patient display 70 is illustrated. Display 70 includes a new patient information entry area 72 and keyboard 54. The user may use keyboard 54 to enter information about the new patient. A similar display may be presented for an existing patient, if the user selects existing patient on the previous display screen 60.

Figure 7:
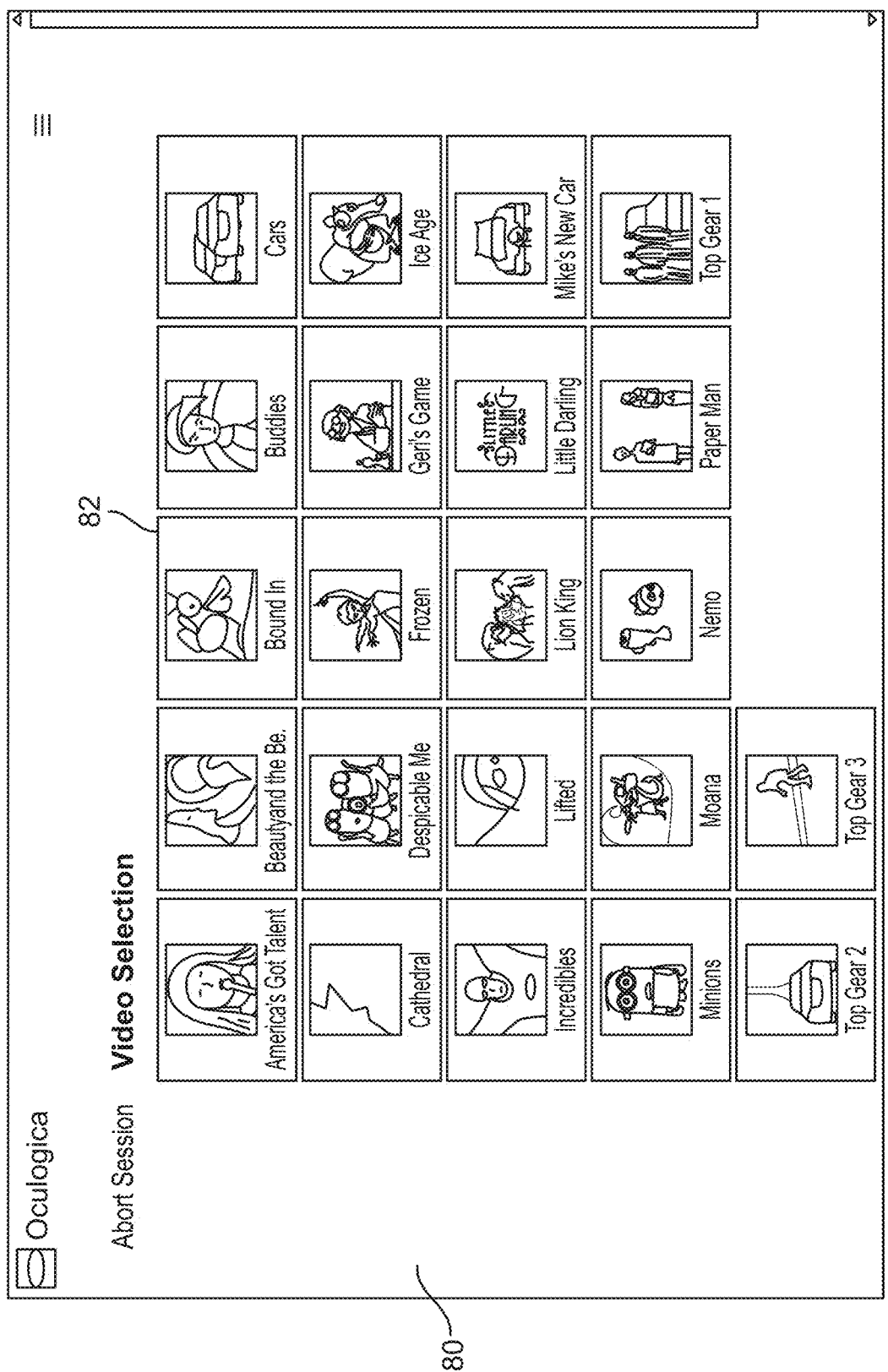
FIG. 7 is a screen shot of a patient video selection display for a stimulus screen of an eye tracking system, according to one embodiment.

FIG. 7 shows a patient video selection display 80, which may be displayed to the patient on stimulus screen 12. Video selection display 80 includes multiple rows and columns of video selection buttons 82, each of which includes an image and title of a video. The patient may select one of the video selection buttons 82 by touching stimulus screen 12.

Figure 8:
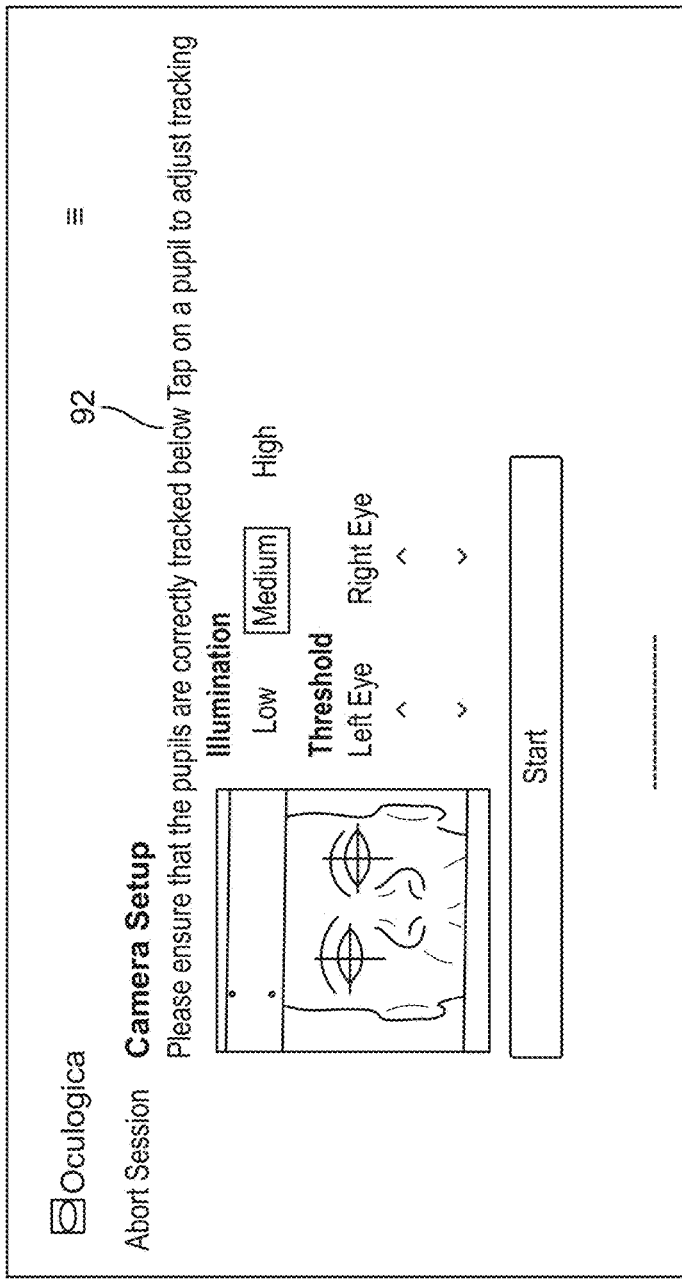
FIG. 8 is a camera setup display for a touchscreen interface of an eye tracking system, according to one embodiment.
Figure 9:
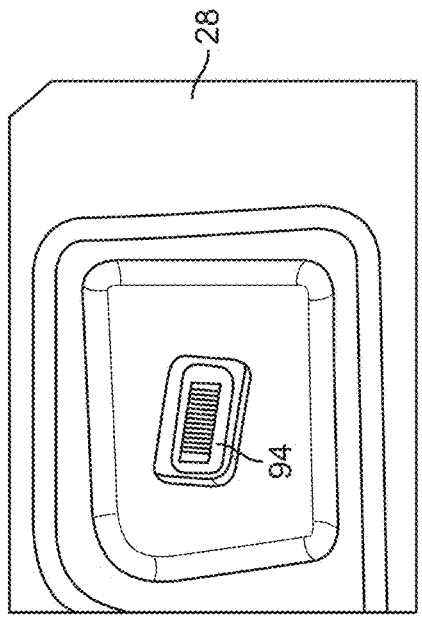
FIG. 9 is a close-up illustration of a camera adjustment knob on a main column of a chassis of the eye tracking system, according to one embodiment.

With reference to FIG. 8, a camera setup display 90 is illustrated. This display 90 may be shown to the user, on touchscreen interface 26, to help the user adjust camera 14. Display 90 may include a camera setup area 92, which may show an image of the patient and information regarding illumination and threshold values. As show in FIG. 9, main column 28 of chassis 20 may include a camera adjustment knob 94 for adjusting focus of camera 14.

Figure 10:
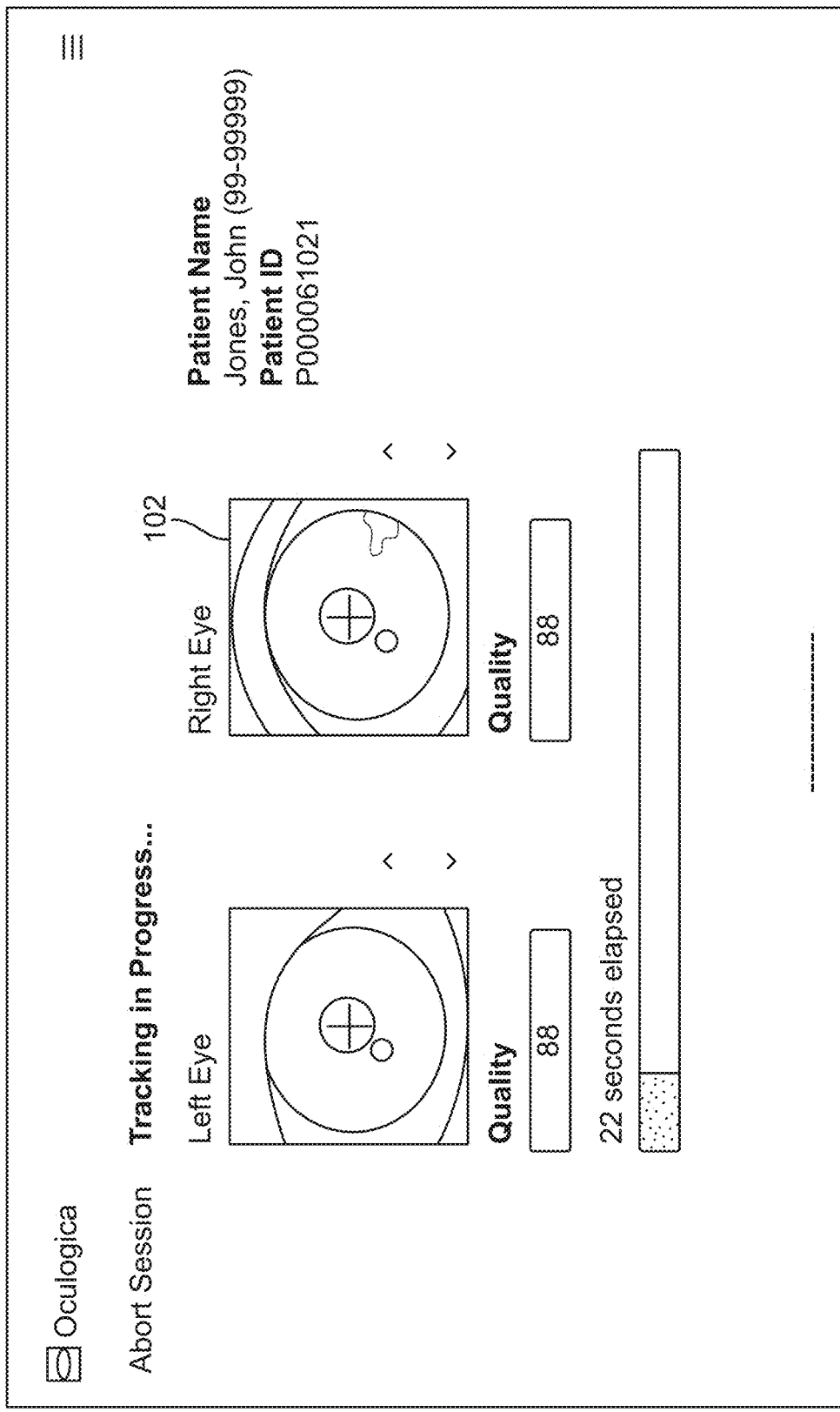
FIG. 10 is a screen shot of a tracking progress display for a touchscreen interface of an eye tracking system, according to one embodiment.

FIG. 10 shows a tracking progress display 100, which also may be shown to the user on touchscreen interface 26. Tracking progress display 100 may include images 102 of the patient's right and left eyes, as well as patient information, tracking quality information, time elapsed for the eye tracking process and/or the like.

Figure 11:
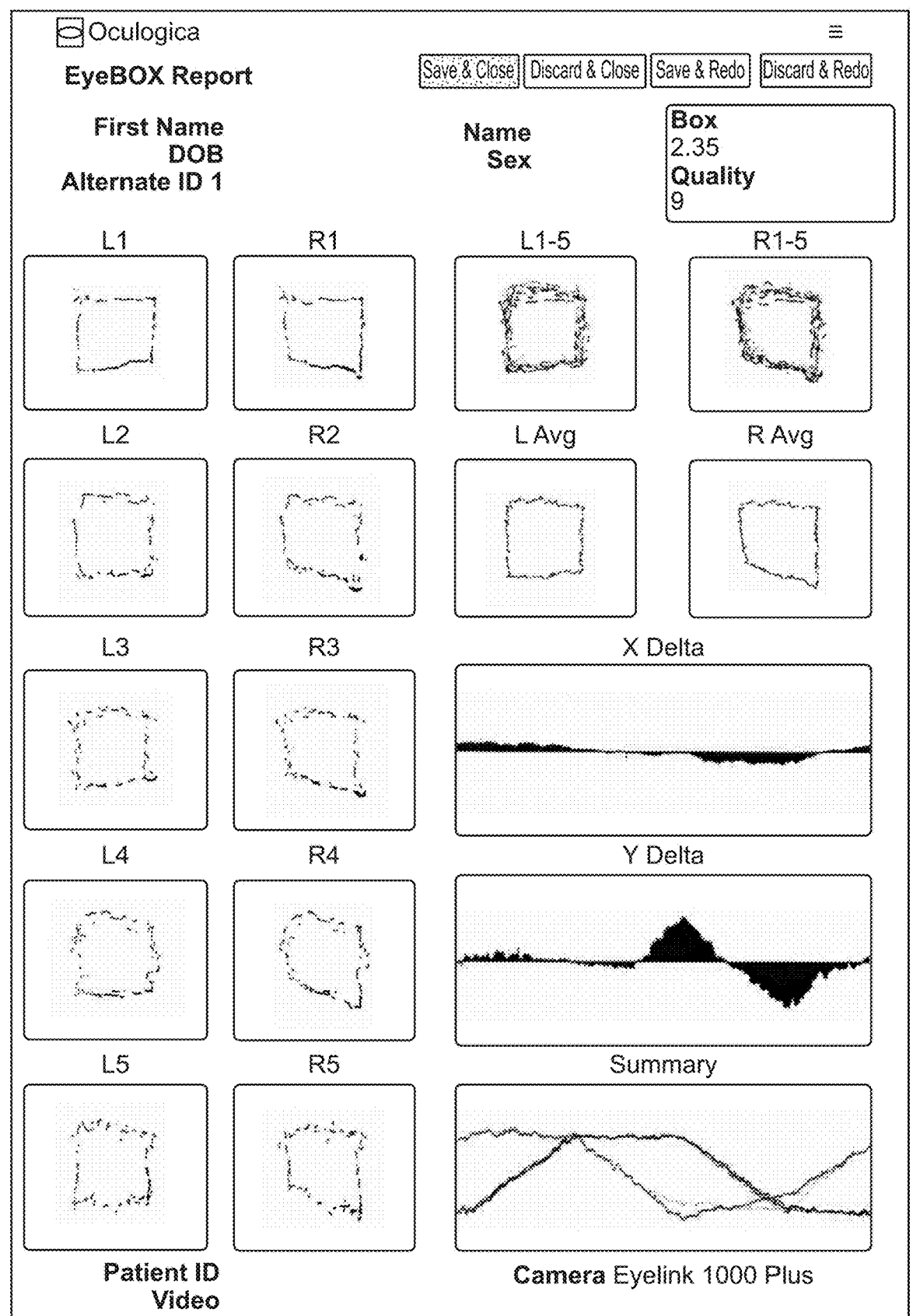
FIG. 11 is a screen shot of an eye tracking report 110 produced by the eye tracking system, according to one embodiment.

Finally, FIG. 11 shows an exemplary embodiment of an eye tracking report 110. Report 110 may include patient information, images representing the eye tracking of the patient, camera information, quality information, a BOX score and/or the like.

The above description is intended to be a complete description of one embodiment of a system and method for measuring eye tracking for one or more diagnostic purposes. It is meant to be a description of examples only and is not intended to limit the scope of the invention.

We claim:

1. A system for measuring eye tracking in a patient and using the measured eye tracking to help diagnose an abnormality, the system comprising:
   a chassis, comprising:
      a main column; and
      a head rest assembly, comprising:
         a stimulus screen for displaying a video to the patient;
         an optical mirror spaced from the stimulus screen;
         an eye tracking camera; and
         at least one forehead rest member for stabilizing the patient's forehead, relative to the stimulus screen;
      a base attached to a bottom of the main column to support the main column;
      an arm extending from the main column to support the head rest assembly and configured and arranged to adjust a position of both the stimulus screen and the at least one forehead rest member;
      a touchscreen interface attached to the main column and configured to provide control of the system to a user;
      a camera computer housed in the main column for controlling the eye tracking camera; and
      a system computer housed in the main column for controlling the stimulus screen, data processing and other functions of the system.
2. The system of claim 1, further comprising an elevator housed in the main column for moving the arm up and down relative to the main column, movement of the arm being configured to adjust the position of both the stimulus screen and the at least one forehead rest member.
3. The system of claim 1, further comprising multiple wheels attached to a bottom of the base to allow the system to be wheeled along the ground, wherein the base and the multiple wheels are sized to fit underneath a patient bed or gurney.

4. The system of claim 3, further comprising a handle attached to the main column for moving the system along the ground.

5. The system of claim 1, wherein the main column of the chassis further includes a slot, wherein the arm moves up and down through the slot to adjust a height of the headrest assembly, and wherein the system further comprises an elevator mechanism in the main column, attached to the arm, to move the arm up and down.

6. The system of claim 1, wherein the main column of the chassis houses multiple additional components, comprising:
   a power supply;
   an elevator mechanism attached to the arm, to move the arm up and down; and
   an isolation transformer.

7. The system of claim 1, wherein the head rest assembly further comprises a chin rest, the head rest assembly being configured to rotate in a horizontal plane and a vertical plane, relative to the arm.

8. The system of claim 7, wherein the head rest assembly including the stimulus screen is configured to rotate in the horizontal plane 90 degrees in either direction, for a total horizontal rotation of 180 degrees, and 90 degrees in the vertical plane in a downward direction, to accommodate supine patients.

9. The system of claim 7, wherein the head rest assembly locks into multiple discrete positions within vertical rotation about the arm.

10. The system of claim 7, further comprising two buttons on the back of the head rest assembly, which are configured to activate solenoids to allow for vertical rotation of the head assembly.

11. The system of claim 1, further comprising two built-in speakers to provide audio to the patient along with video on the stimulus screen.

12. The system of claim 1, wherein the system computer is configured to generate a score describing the eye tracking of the patient.

13. The system of claim 12, wherein the score ranges from 0 to 20, wherein the score is interpreted as a binary classification for eye movement abnormalities, wherein if the score is equal to or greater than 10, that represents a positive result (abnormality present), and wherein if the score is below 10, that represents a negative result (no abnormality present).

14. A method for measuring eye tracking in a patient using an eye tracking system, the method comprising:
   receiving user information input by a user via a touchscreen interface of the eye tracking system;
   receiving patient information input by the user via the touchscreen interface;
   receiving a video selection from the patient via a stimulus screen of the eye tracking system;
   displaying a video to the patient on the stimulus screen, according to the video selection;
   tracking movement of the patient's eyes during display of the video via an eye tracking camera of the eye tracking system; and
   generating, with a computer processor of the eye tracking system, a box score representing an ability of the patient's eyes to track the video.

15. The method of claim 14, wherein the box score ranges from 0 to 20, wherein the box score is interpreted as a binary classification for eye movement abnormalities, wherein if the box score is equal to or greater than 10, that represents a positive result (abnormality present), and wherein if the box score is below 10, that represents a negative result (no abnormality present).

16. The method of claim 14, further comprising:
   receiving an instruction from the user to adjust a height of a head rest assembly of the eye tracking system; and
   moving an arm attaching the head rest assembly to a main column of the eye tracking system at least one of up or down, in response to the instruction.

17. The method of claim 14, further comprising:
   receiving an instruction from the user to adjust a vertical orientation of a head rest assembly of the eye tracking system; and
   rotating the head rest assembly in a vertical plane relative to an arm attaching the head rest assembly to a main column of the eye tracking system, in response to the instruction.

18. The method of claim 14, further comprising:
   receiving an instruction from the user to adjust a horizontal orientation of a head rest assembly of the eye tracking system; and
   rotating the head rest assembly in a horizontal plane relative to an arm attaching the head rest assembly to a main column of the eye tracking system, in response to the instruction.

19. The method of claim 14, further comprising evaluating the differences in movement between a right eye and a left eye.

* * * * *